United States Patent
Dubrul et al.

(10) Patent No.: US 7,011,654 B2
(45) Date of Patent: Mar. 14, 2006

(54) DILATING AND SUPPORT APPARATUS WITH DISEASE INHIBITORS AND METHODS FOR USE

(75) Inventors: William Richard Dubrul, Redwood City, CA (US); Richard E Fulton, Grand Junction, CO (US)

(73) Assignee: Artemis Medical, Inc., Hayward, CA (US)

(*) Notice: Subject to any disclaimer, the term of this patent is extended or adjusted under 35 U.S.C. 154(b) by 0 days.

(21) Appl. No.: 09/781,721

(22) Filed: Feb. 12, 2001

(65) Prior Publication Data

US 2001/0027307 A1 Oct. 4, 2001

Related U.S. Application Data

(62) Division of application No. 09/298,279, filed on Apr. 23, 1999, now Pat. No. 6,450,989.

(60) Provisional application No. 60/115,548, filed on Jan. 12, 1999, provisional application No. 60/095,106, filed on Aug. 3, 1998, and provisional application No. 60/083,178, filed on Apr. 27, 1998.

(51) Int. Cl.
*A61M 31/00* (2006.01)
*A61M 29/00* (2006.01)
*A61N 1/30* (2006.01)

(52) U.S. Cl. .................. 604/508; 604/507; 604/509; 604/104; 604/501; 604/21; 606/194

(58) Field of Classification Search .............. 604/96.01, 604/500, 501, 20, 507, 508, 509, 103.01, 604/103.02, 103.05–103.09, 104, 107–109, 604/21; 606/200, 191–192, 194; 623/1.11, 623/1.42–1.43, 1.45–1.46
See application file for complete search history.

(56) References Cited

U.S. PATENT DOCUMENTS

| | | | |
|---|---|---|---|
| 3,996,938 A | 12/1976 | Clark, III |
| 4,425,908 A | 1/1984 | Simon |
| 4,611,594 A | 9/1986 | Grayhack et al. |
| 4,650,466 A | 3/1987 | Luther |
| 5,030,201 A | 7/1991 | Palestrant |
| 5,102,415 A | 4/1992 | Guenther et al. |
| 5,183,464 A | 2/1993 | Dubrul et al. |
| 5,192,297 A | 3/1993 | Hull |
| 5,197,977 A | 3/1993 | Hoffman, Jr. et al. |
| 5,222,971 A | 6/1993 | Willard et al. |
| 5,318,531 A | 6/1994 | Leone |

(Continued)

FOREIGN PATENT DOCUMENTS

| DE | 39 13935 | 4/1989 |
|---|---|---|
| GB | 2020557 | 11/1979 |

*Primary Examiner*—Nicholas D. Lucchesi
*Assistant Examiner*—Catherine S. Williams
(74) *Attorney, Agent, or Firm*—James F. Hann; Haynes Boffel & Wolfeld LLP

(57) ABSTRACT

A dilating and support apparatus with disease inhibitors and methods for use is disclosed that is particularly useful for repairing and/or serving as a conduit for body passageways that require reinforcement, dilatation, disease prevention or the like. Such apparatuses are utilized to deliver a therapy, that therapy being from a family of devices, drugs, or any of a variety of other elements to a specific location within the body. The instant disclosure provides a system of combining a novel radial deployment and/or drug delivery therapy with existing balloon dilatation therapy into one device. This combination will yield a significant decrease in cost to the healthcare system as well as providing a therapy to the patient with increased safety and efficacy. Further, the instant invention provides a novel and improved platform for synthetic/tissue interface between the device and the body.

6 Claims, 4 Drawing Sheets

U.S. PATENT DOCUMENTS

| | | | | |
|---|---|---|---|---|
| 5,370,660 A | | 12/1994 | Weinstein et al. | |
| 5,382,259 A | | 1/1995 | Phelps et al. | |
| 5,431,676 A | | 7/1995 | Dubrul et al. | |
| 5,454,790 A | | 10/1995 | Dubrul | |
| 5,507,724 A | | 4/1996 | Hofman et al. | |
| 5,562,725 A | | 10/1996 | Schmitt et al. | |
| 5,591,199 A | | 1/1997 | Porter et al. | |
| 5,591,227 A | * | 1/1997 | Dinh et al. | 606/195 |
| 5,643,282 A | | 7/1997 | Kieturakis | |
| 5,749,883 A | | 5/1998 | Halpern | |
| 5,749,890 A | * | 5/1998 | Shaknovich | 606/198 |
| 5,769,871 A | | 6/1998 | Mer Kelly et al. | |
| 5,792,157 A | | 8/1998 | Mische et al. | |
| 5,796,045 A | | 8/1998 | Lancien et al. | |
| 5,807,306 A | * | 9/1998 | Shapland et al. | 604/21 |
| 5,810,767 A | * | 9/1998 | Klein | 604/509 |
| 5,827,324 A | | 10/1998 | Cassell et al. | |
| 5,851,210 A | | 12/1998 | Torossian | |
| 5,868,708 A | | 2/1999 | Hart et al. | |
| 5,871,535 A | * | 2/1999 | Wolff et al. | 128/898 |
| 5,882,335 A | | 3/1999 | Leone et al. | |
| 5,897,567 A | | 4/1999 | Ressemann et al. | |
| 5,928,260 A | | 7/1999 | Chin et al. | |
| 5,941,869 A | | 8/1999 | Patterson et al. | |
| 6,027,520 A | | 2/2000 | Tsugita et al. | |
| 6,156,005 A | * | 12/2000 | Theron | 604/101.05 |
| 6,219,577 B1 | * | 4/2001 | Brown et al. | 604/20 |
| 6,238,412 B1 | | 5/2001 | Dubrul et al. | |
| 6,361,545 B1 | | 3/2002 | Macoviak et al. | |
| 6,635,068 B1 | | 10/2003 | Dubrul et al. | |
| 2002/0045916 A1 | | 4/2002 | Gray et al. | |

* cited by examiner

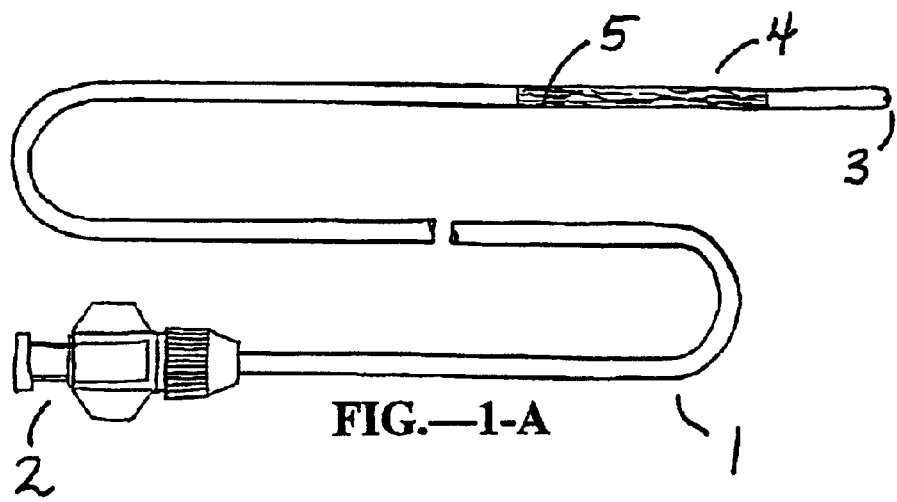
FIG.—1-A
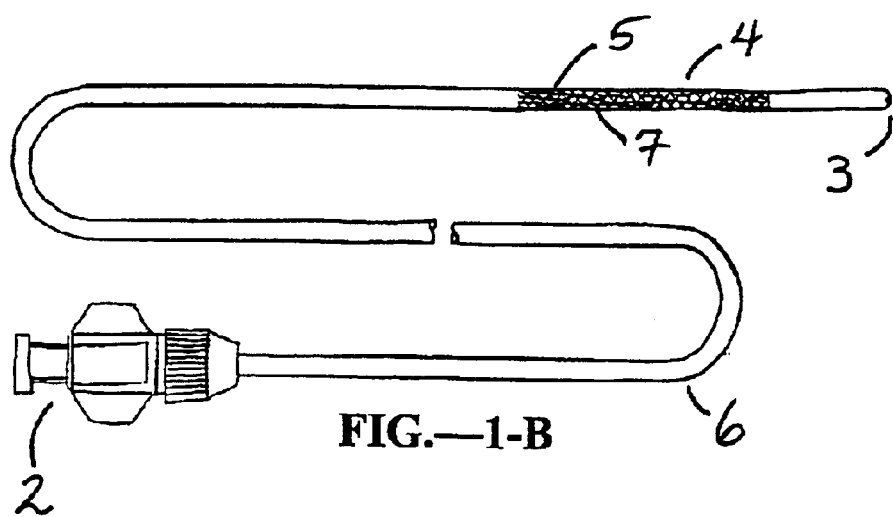
FIG.—1-B

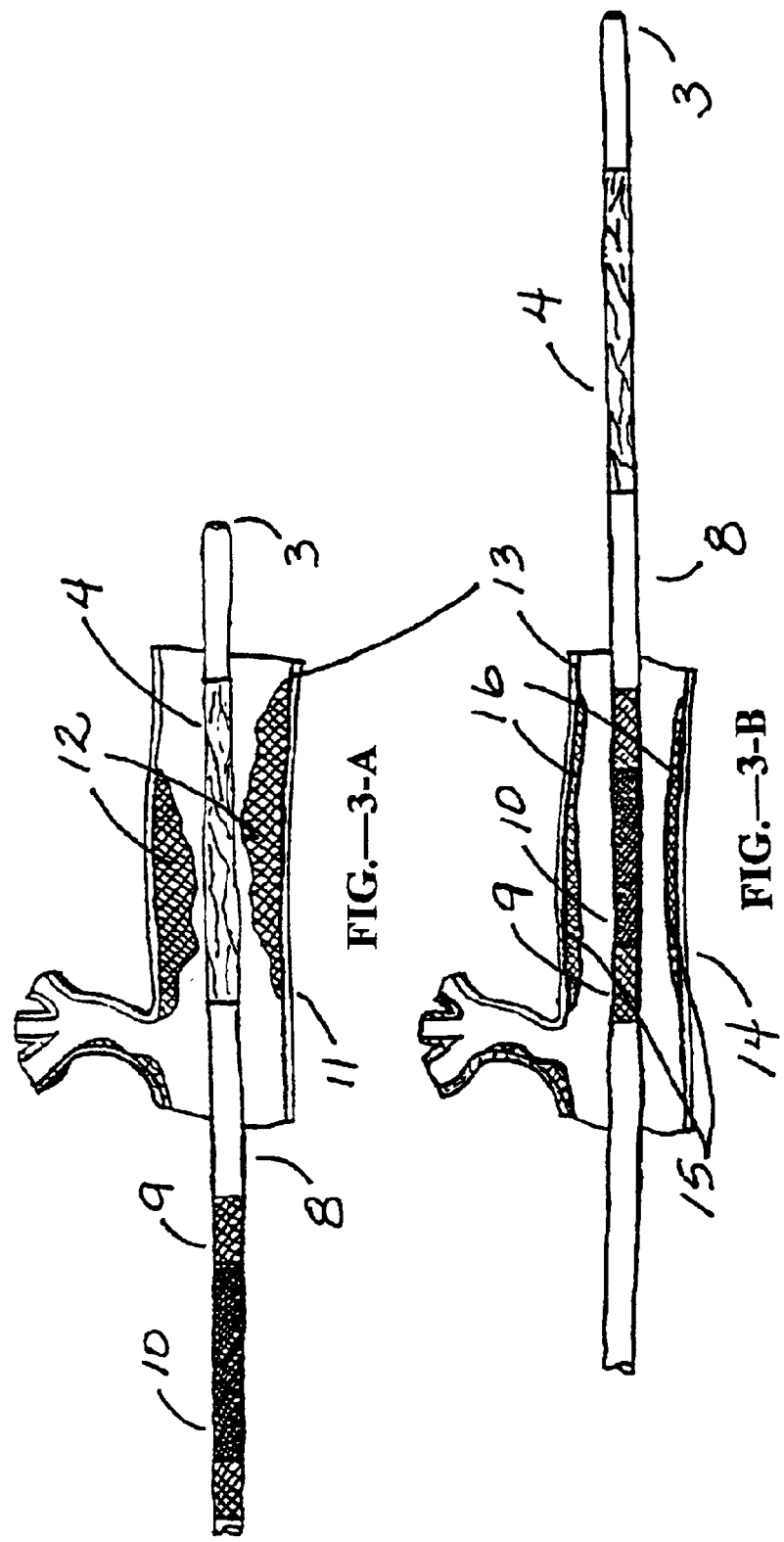

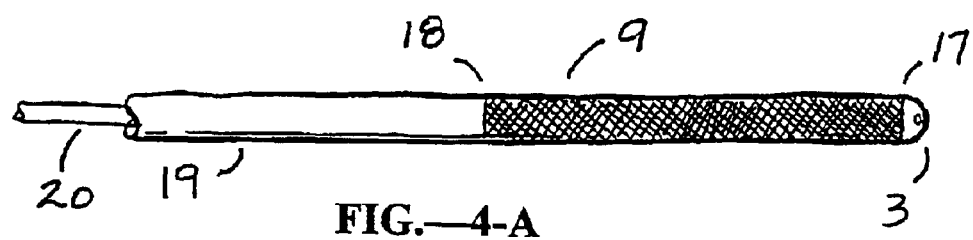
FIG.—4-A
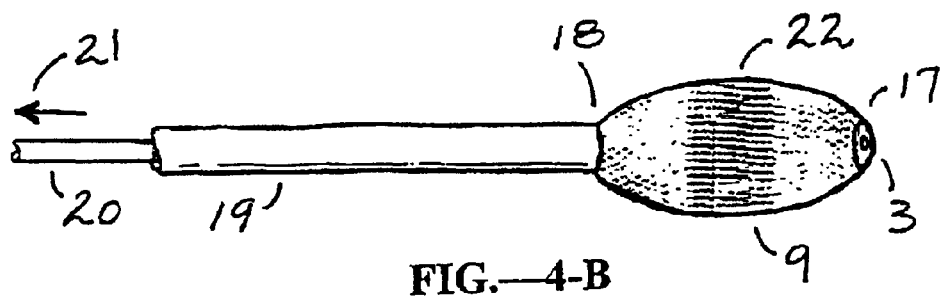
FIG.—4-B

DILATING AND SUPPORT APPARATUS WITH DISEASE INHIBITORS AND METHODS FOR USE

CROSS REFERENCE TO RELATED APPLICATION

This application is a division of U.S. patent application Ser. No. 09/298,279 filed Apr. 23, 1999, which claims the benefit of the following provisional patent applications: application No. 60/083,178 filed Apr. 27, 1998; application No. 60/095,106 filed Aug. 3, 1998; and application No. 60/115,548 filed Jan. 12, 1999, the disclosures of which are incorporated by reference.

FIELD OF THE INVENTION

The present invention relates to medical devices and their methods of use. More specifically, the present invention relates to devices which are particularly useful for repairing and/or serving as a conduit for body passageways requiring reinforcement, dilatation, disease prevention or the like. Such devices are utilized to deliver a therapy, that therapy being from a family of devices, drugs, or any of a variety of other elements to a specific location within the body.

The present invention provides a system of combining a novel deployment and/or drug delivery therapy with existing balloon dilatation therapy into one device. This combination will yield a significant decrease in cost to the healthcare system as well as providing a therapy to the patient with increased safety and efficacy. Further, the instant invention provides a novel and improved platform for synthetic/tissue interface between the device and the body.

BACKGROUND OF THE INVENTION

Occlusive vascular disease is a common ailment in people resulting in enormous costs to the health care especially with the 'Graying of America' due to the baby boomers of the 50's. The common procedure of dilatation of these occluded vessels of the body has been studied for several years and many techniques (devices and methods) have been studied and practiced. One of the more common techniques is one referred to as balloon angioplasty or Percutaneous Transluminal Angioplasty (PTA). PTA is the most common treatment of atherosclerotic plaque deposition. However, this PTA has significant drawbacks; some of which are the cost of the catheter and the potential for the stenotic vessel to 'recoil' or narrow back down after the procedure. Hence scaffolds (stents or stent-grafts) have been designed that stay in place to keep the vessel 'propped open' after dilatation. Other significant design changes have occurred with PTA such as the use of drugs pre, during and post dilation. Balloons have been designed with permeable membranes to aid with this delivery. Further, the balloons have been designed with imperfections in the surface of the balloon that aid in breaking up the plaque matrix during dilation (tiny cutters for example have been impregnated into the exterior wall of the balloon). Further energy dispersal systems have been employed to deliver energy to the site pre, during or post therapy (e.g. radiation, electrical stimulation, RF, etc.). Even further, extravagant perfusion systems have been developed with the dilatation systems so that blood can flow during the therapy. All of these proposed 'enhancements' add significantly to the cost and complexity of the dilation or stent device. The present invention allows all of these enhancements to occur with an overall reduction in the manufacturing resources required for the device since one device/catheter is required as opposed to two or more. Even more important, is the time efficiencies created during the procedure by obviating the need to exchange the devices/catheters to perform the acts which may include angioplasty, stent deployment, and drug delivery. Safety to the patient is enhanced, as well, by obviating the time consuming exchanges and diminishing the time of the procedure.

Also, despite the evolution of a variety of mechanical techniques and adjunctive therapies, approximately 30–45% of patients treated with balloon angioplasty will develop a recurrent stenosis within six months. Stenting of the lesion will decrease the re-stenosis rate to 20–30%, although with additional cost and risks. The cost of treating patients with re-stenosis which require another revascularization procedure or additional therapy and has been estimated to cost 2500 lives and $4 billion. Re-stenosis is a complex process, which is due to some combination of suboptimal results, acute mechanical recoil, thrombosis and platelet deposition, smooth muscle proliferation, extracellular matrix production, and geometric remodeling as well as other reasons not reported here. Because of the improvement in the re-stenosis rate with intraluminal stents, it is likely that stenting prevents the mechanical events which contribute to re-stenosis, i.e., suboptimal results, acute mechanical recoil, and geometric remodeling. However, stenting has been shown to accelerate or incite smooth muscle proliferation, thrombosis and platelet deposition, and matrix production. These events may be grouped together and referred to as neointimal hyperplasia. Exuberant neointimal hyperplasia may lead to stenosis within a stent, referred to as in-stent re-stenosis. Therefore, stents may improve the re-stenosis rate, but at a significant financial cost, potential risk to the patient, and a possibility of developing in-tent stenosis. Hence, a novel invention that allows safer, less expensive and more efficacious dilatation and stent deployment is described in the present invention.

As stated, stenting is not the cure all. Moreover, pharmacological therapy has not been shown efficacious in significantly reducing neointimal hyperplasia, for several different reasons. One reason is related to the systemic intolerances of doses required to achieve local beneficial effects within the arterial wall. A local drug delivery device which would deliver higher drug concentration to the target while avoiding systemic toxicity's or side effects would be advantageous. In fact there are several patented local drug delivery devices, including balloon catheters, coated stents, and even needle catheters. However, most are plagued with the rather uniform problem of low transfer efficiency, rapid washout/poor retention, and the potential of additional vessel injury. Most also require insertion of a separate and specialized catheter separate from the angioplasty balloon catheter, which is a time consuming, costly, and potentially a risky maneuver.

There are many techniques and devices known in the art for removing blockages, repairing occlusions and otherwise preventing or treating disease in the passageways of the human body. Further, many approaches exist to treat the synthetic/tissue interface that exists when using medical devices and implants in the body. However, there is a continuing need for improved devices to meet at least the following objectives.

The first objective is to reduce cost. This is particularly important in recent years where it is clear for safety and sanitary reasons that these will be single use devices. A device, even though it performs a function in some improved manner, will not be widely used if it is considerably more costly than the alternatives available.

A second objective is to provide a device that is simple to use and in a very real sense simple to understand. This will encourage its adoption and use by medical personnel. It will also tend to keep cost low.

The third objective is to provide a device that entails a procedure with which the medical profession is familiar so that the skills that have been learned from previous experience will continue to have applicability.

A fourth objective relates to the effectiveness and thoroughness with which the blockage is removed. It is important that a maximum amount of the blockage be removed; recognizing that no device is likely to provide one hundred percent removal.

A fifth objective concerns safety; a matter which is often so critical as to trump the other considerations. It is important to avoid tissue trauma. In many circumstances, it is critically important to avoid breaking up a blockage in a fashion that leads to flushing elements of the blockage throughout the body involved.

There are trade-offs in design considerations to achieve the above five interrelated objectives. Extreme simplicity and a very simple procedure might over compromise safety. Addressing all of these considerations calls for some trade-off between the objectives.

Accordingly, a major object of this invention is to provide an improved device for treatment or prevention of disease of a body passageway, which achieves the objectives of, reduced cost, enhanced simplicity, a standard procedure, high effectiveness and a high degree of safety. Most particularly, it is an object of the present invention to achieve these objectives with an enhanced trade-off value for the combined objectives.

BRIEF DESCRIPTION

A novel device description is set forth in the instant invention that allows for treatment of fully or partially occluded vessels within the body; usually those vessels being blood vessels. In brief, the instant invention allows multiple therapies to be provided with a single device. One embodiment of the instant invention is to provide a single device/catheter/guide wire that allows for balloon angioplasty of a stenotic lesion in the vasculature and deployment of a device for propping open the vessel with that same device. This is often referred to as an endoprosthesis, but more frequently referred to as a stent or stent-graft. Usually stenosis of a blood vessel is treated by placing a balloon in the narrowed/stenosed area of the vessel and expanding the balloon, which subsequently expands the narrowed vessel, at least temporarily or partly. This balloon expansion is referred to as balloon angioplasty. Unfortunately, too often after balloon angioplasty, the vessel returns to its original 'narrowed' condition. This is referred to as recoil, if it occurs acutely. Subacute or late narrowing may be secondary to restenosis, a complex process described more fully elsewhere in this document. These processes occur in a large percentage of 'ballooned' vessels, sometimes upward of fifty percent. Because of this limited long-term success, balloon angioplasty is frequently used in addition to, or in conjunction with, other therapies such as placement of a stent, stent-graft, or subsequent drug delivery to the area of stenosis or re-stenosis. The additional therapies will hopefully prevent the re-closure of the vessel after balloon angioplasty. These subsequent therapies require the addition of new devices after balloon angioplasty. Hence, it is standard procedure to remove the angioplasty device only to replace it with another device that either delivers the stent or stent-graft, and even another device, which delivers the drug or other therapy. Hence it is the preferred embodiment of the instant invention to provide a device that can expand the vessel via a balloon angioplasty device, but also provide a system that can simultaneously or subsequently deliver a therapy such as a stent or stent-graft or deliver agents/drugs without the removal of the original angioplasty device/catheter.

Conversely, a novel therapeutic device is described in the instant invention that can dilate the narrowed vessel without the use of a balloon and can then deploy a stent or stent-graft with a balloon or with another novel mechanism on the same device.

Further, another preferred embodiment of the instant invention allows for a therapeutic delivery of a drug or other agent to tissue to prevent or treat disease. In particular, during balloon angioplasty, this is accomplished without an additional device being used for this therapy.

The instant invention is primarily, though not exclusively, oriented to the use of technology referred to as tubular braid or braided sleeving. The basic design of tubular braid is well defined later in the patent under a particular 'comments' section entitled *The Tubular Braid or Braided Sleeve Element*.

Description of Backgound Art

Intraluminal devices or endovascular prostheses are known for treating stenosis, stricture, aneurysm conditions and the like. Often these devices are implanted or used via LIS (Least Invasive Surgery); whereby a small percutaneous access into the vessel is accomplished (usually remote to the diseased area). Alternatively, they are installed via an 'open surgery' approach. Advantages of the LIS approach (over conventional surgery) are significant from a cost as well as a patient care and recovery point of view. Balloon catheters have found an increased use in medical procedures such as percutaneous transluminal angioplasty (PTA), percutaneous translurninal nephrostomy, ureteral dilatation, biliary duct dilatation, percutaneous transluminal renal angioplasty and the like. Intellectual property regarding balloon dilatation is extensive and shall not be exhaustively reported here, however, certain patents deemed relative are described. Gruntzig et al in U.S. Pat. No. 4,195,637 and Simpson et al in U.S. Pat. No. 4,323,071 are two very well known patents that have been said to initiate the onslaught of intellectual property that is realized with balloon angioplasty. These two patents describe initial intellectual property associated with balloon angioplasty and are often referenced as a basis for such discussions, however have little relevancy to the inventions disclosed herein except for that basis. U.S. Pat. Nos. 4,448,195, 4,637,396, 4,608,984 and 4,646,742 describe balloons reinforced with fabric and/or multi-layer construction to increase strength and control expansion. Levi U.S. Pat. No. 4,490.421 is a well-discussed patent that disclosed the use of PET materials in the fabrication of angioplasty balloons that allow high pressures without rupture. Stents and stent-grafts have in-depth coverage in the intellectual forefront as well. A predominant stent patent by Palmaz, U.S. Pat. No. 4,776,337 discloses a well-known device frequently referred to as a Self-Expanding Stent. Self-Expanding Stents have come of favor recently over balloon expandable stents for reasons not completely understood by the author, but likely due to the perceived decrease in effort to deploy the stent since there is only the initial balloon dilatation and then stent deployment instead of balloon dilatation, and balloon dilation/stent deployment a second time to implant the stent or stent-graft. However, multiple catheter exchanges must be made to dilate the lesion with the angioplasty catheter, deliver the self expanding stent with another catheter or delivery device, and then reinsert the angioplasty balloon catheter to tack the stent down properly. Further, because stent placement is still relatively new in medicine, the interventionalist is always left with the question of long-term reliability (with regard to restenosis) of all stent placements. Intraluminal scaffolding devices such as stents are often used in combination with grafts and vice versa The graft is usually, but not always a an elastic or inelastic material and often a textile/fabric type material that is used to cover a greater area of the scaffolding as well as aid in neo-intimal formation after placement. Further, the two (stents and grafts) are often designed into one device called a stent-graft.

One embodiment of the present invention allows balloon dilation and stent deployment to be accomplished with one device. In and of itself this technique as well as other inventions have tried to accomplish the same, but have been met with limited success. LeVeen, LeVeen and LeVeen in U.S. Pat. No. 4,404,971 describe a dual balloon catheter to control bleeding to facilitate surgical closure of the blood vessel. Taking this multiple balloon concept further, Hegde et al in U.S. Pat. No. 5,725,535 describe a method for using a multiple balloon catheter that allows balloon dilatation of the stricture and then stent deployment using the same catheter. However, the resulting multiple balloon device is more than complicated and Hegde et al disclose a method for a complex and expensive device. Further, using balloons for dilatation and for stent deployment require a significant amount of time for inflation/filling and subsequent deflation/un-filling of the balloons. The rate of inflation and deflation of the balloons bears directly on the stress induced on the heart during the procedure. In U.S. Pat. No. 5,725,535, Hegde et al describes the multiple balloon device in detail in the body as well as in the claims. However, in addition to the inflation and deflation times mentioned above, the device described in this patent has the obvious drawbacks of requiring a separate lumen for each balloon. In addition to increasing the cost of manufacture, this requirement requires the overall diameter of the catheter to be increased. Marin and Marin in U.S. Pat. No. 5,456,694 describe an extravagant catheter similar to the Hegde patent whereby multiple balloons are used to accomplish the same as in the Hegde patents. Marin and Marin disclose a guiding sheath in cooperation with their multiple balloon system that has a variable stiffness that is made available through their design that reportably decreases trauma to the patient. Marin and Marin recognize the limitations of multiple balloons in their design and make mention of alternative mechanical linkages to deploy the stents. These linkages are described in Marin's U.S. Pat. Nos. 5,618,300 and 5,443,477. Marin and Marin indeed describe an alternative mechanical linkage device for stent deployment in these subsequent patents, however again only at the cost of losing cost effectiveness in the manufacture of the catheter as well as the potential increase in size of the diameters of the catheters and potential flexibility of the catheter/device. Further, in U.S. Pat. No. 4,585,000, Harold Hershenson describes a mechanical linkage type dilator that is similar to that of Marin and Marin in that it is complicated for manufacture and difficult for size reduction which is of paramount importance. Further, all of these mechanical linkages lend themselves to an inflexibility characteristic. Because of the tortuous paths realized in the vasculature, flexibility of the catheter/device is critical. It is often the case that narrowing of vessels in the body often occur at tortuous curves or bifurcations similar to shallows in a stream or river.

Hence in the present invention, described herein, the inventors describe a multiple use device/catheter, that can be made in a low cost manufacturing environment while keeping diameter of the device to a minimum, but keeping safety and efficacy to the patient at a maximum. The present invention utilizes a manufacturing technique known as tubular braid or braided sleeving to accomplish either dilatation or stent deployment. The instant invention may be used with a dilation balloon on the device in combination with the tubular braid. When the tubular braid is put into compression, the braid expands radially for dilation and/or stent deployment. Further, the inventors disclose a novel device and method for using a single device for dilatation and stent deployment without the need for balloons at all. Embodiments are described which will provide the capability of balloon dilation and deployment of an expandable stent or a self-expanding stent.

Additionally, the inventors disclose the use of tubular braid as a device to deliver drug/agent/therapy to passageways as well.

The use of tubular braid for use in the tubular vessels of the body is not new and is described in several issued U.S. Patents. Anderson et al in U.S. Pat. No. 4,706,670 describes a unique use of tubular braid in conjunction with balloon angioplasty. In this disclosure, Anderson et al describe the use of tubular braid that is molded into an elastomeric catheter shaft so that upon expansion of the catheter from within, the shaft only expands and dilates to a fixed diameter that is predetermined by the inelastic tubular braid filaments within the walls of the catheter. When pressure is removed from the device the diameter contracts back to its original, 'undilated' diameter. In U.S. Pat. No. 4,650,466, Ronald Luther describes a tubular braided device for use in angioplasty where the expanded braid is used for removal and trapping of debris during said angioplasty. In U.S. Pat. No. 4,572,186, Gould et al describe a dilation catheter using tubular braid. Gould describes the objectives of his inventions to replace angioplasty balloon for providing improved dilating forces, decreased costs, and radiopacity and improve upon balloon dilation limitations such as the forces realized with balloon catheters are not realized until the balloon is almost filled with filling agent. Hence Gould describes a dilatation device using braid that does not necessarily go from a very small diameter to a very large diameter that is evidenced by these objects as well as are realized in his illustrations. Further, and again, Gould did not invent the use of the tubular braid in conjunction with other dilation or deployment. In fact due to the description that the author gives in the patent, it is likely that the inventors could not determine a design that would transmit significant force to a blood vessel so as to actually dilate the vessel and the underlying stenotic, atheroma/plaque which tends to be a hard and sinuous material that is not too receptive to dilatation without constraining his design to small incremental dilations from said small catheter shaft to only a slightly larger diameter shaft after deployment The same Applicant with a different Inventor, Richard Hillstead in U.S. Pat. No. 4,921,484 describes a Mesh Balloon Catheter device. Hillstead discusses the use of the tubular braid for stent deployment, filtering and centering characteristics in the body of his disclosure, but limits his invention to drainage of the device wherein fluid accumulation occurs in the expanded tubular braid or with other flushing lumens there-through with regard to using the device for the compression and or removal of material during an angioplasty. Certainly nowhere does Hillstead recognize the advantage of combining the tubular braid with balloon angioplasty, nor it is obvious to anyone normally skilled in the art. Hillstead describes an intricate device for expanding the tubular braid.

The mechanism described in the Hillstead patent misses the importance of decreased diameter of the catheter, decreased manufacturing costs, the importance of physical flexibility of the catheter and importantly the invention of coupling the more than one tubular braid mechanism with another or with a balloon dilator to decrease the overall cost of the devices required for dilatation and stent placement or the increase in safety and efficacy that such a design gives to the patient. Wholey et al in U.S. Pat. No. 4,723,549 describes a method and apparatus for dilating blood vessels. Wholey describes a tubular braid being used as a filter or trap to collect emboli that may become dislodged during the intervention. A balloon is used to expand tubular braid that remains expanded as a filter or trap during the PTA procedure. Further, in U.S. Pat. No. 5,034,001, Garrison et al discloses an angioplasty device with a temporary stent that may be fabricated from tubular braid. This temporary stent in the Garrison et al patent is used to help prevent the problems that are realized with instantaneous recoil subsequent to angioplasty/balloon dilatation.

In fact, the present inventors have several patents some of which have issued and some of which are pending that use the tubular braids for medical devices. In U.S. Pat. No. 5,498, 5,280,273, 5,713,848 and Continuation of these issued patents, Ser. No. 098/005,217, the current inventor discloses the use of tubular braid as an occluder and as a filter and trap for dislodged emboli and blood particulate. Further, the current inventor in U.S. Pat. 5,431,676 uses tubular braid to facilitate a radially expanding trocar. Even further, the current inventors in pending U.S. and PCT submissions (U.S. Ser. No. 09/063,735 and PCT/US Ser. No. 98/08194) disclose tubular braid in the fabrication of embolic containment devices as well as tubular braid use for a bifurcated stent. Further yet, the current inventors use tubular braid in the design and disclosure of devices and methods for entrapping, occlusion, flow direction, tensioning and/or anchoring devices in U.S. Ser. Nos. 09/248,08809/248,083 and PCT/US Nos. 99/02856 and 99/02853.

However, none of the references mentioned above disclose a new device that can be used as a combination dilatation device and stent deployment device that allows increase patient safety and efficacy with an overall reduction in the manufacturing costs and complexity of the combined device or its use by the physician as does the novel invention disclosed herein.

Turning now to another embodiment of the instant invention, that of utilizing the tubular braid in conjunction with an angioplasty balloon (or other dilatation means) for concurrent balloon angioplasty and drug delivery/therapy. This instant invention uses a tubular braid or other similar material that may have an absorbent nature such as Dacron, cotton etc. The absorbent material is placed over a balloon or other dilation device. Prior to placing the balloon into the diseased lesion, the absorbable material is allowed to absorb a therapeutic agent into the individual filaments or in between the filaments and the outer wall of the balloon or other dilatation device. When the dilatation device is placed into the constricted area/lesion of the vessel and the dilated, the drug or other agent is then driven into the vessel wall at the site of the lesion, where it is needed most. Further, the covering material, such as the tubular braid, will act as a means for penetrating the lesion and potentially breaking up the plaque matrix that exists there. Certainly, the drug/agent/therapy will at very least be delivered into the lesion/diseased site, again where it is need most.

U.S. Pat. No. 4,994,033 by Shockey describes an intravascular drug delivery dilatation catheter that disclosed a plurality of minute holes within a set of balloons for subsequent delivery of a drug during angioplasty. However, Shockey et al describes a device that is costly and complicated to manufacture. Wolinsky et al in U.S. Pat. No. 5,087,244 describes a method and catheter with minute holes (approximately 25 microns) through the balloon wall as well for concurrent drug delivery during angioplasty. The repeatability of the sized 25 micron holes in the balloon coupled with the potential restrictions of the drug used for perfusion through these holes lend itself to these disadvantages. In U.S. Pat. No. 5,279,565, Klein et al describes a device and method for infusing an agent to the treatment site as well. Klein et al discloses a rather complex device that would lend itself to costly manufacture if it would be put to practice. Fahrad Khosravi in U.S. Pat. No. 5,415,637 discloses a temporary stenting device with drug delivery capabilities. In his disclosure, Khosravi describes a device that will deliver drugs while propping open a narrowed vessel using an elaborate set of hypotubes with holes drilled in them. As compared with the instant invention, this device will greatly exceed manufacturing costs as well as decrease flexibility of the catheter, which described earlier, is of paramount importance.

The use of drug/agent/therapy devices to be used concurrently with angioplasty has been studied significantly due to the frequent re-stenosis that occurs. The addition of stents to help prevent this re-stenosis has merit and is gaining favor quickly, but does not stop re-stenosis and adds significantly to the treatment costs. In fact, significant development has occurred that deliver drug/agents/therapy to stents, again to prevent re-stenosis. The use of drugs to help prevent re-stenosis shows great value. Stephen R. Bailey reports upon the significant development and reasons for such development in his article entitled Local Drug Delivery: Current Applications, published in *Progress in Cardiovascular Diseases,* Vol. 40, No. 2 (September/October), 1997:pp183–204. In fact, this is merely one several publications regarding the developments and research in this regard.

The drug or therapeutic agent delivery system of the instant invention similarly to the aforementioned and novel dilatation system of this patent uses a very 'manufacturing friendly' process that will allow simple fabrication on a production basis. Further and like the aforementioned dilatation system, this drug or agent delivery system yields characteristics that allow for high safety and efficacy to the patient while minimizing the efforts and time of the clinician.

The five objectives first described in the BACKGROUND OF THE INVENTION are important to a successful invention in today's complicated medical device industry and health care arena and bear repeating. They are reducing cost and complexity, using a procedure that the healthcare professional is familiar with and maximizing/optimizing safety and efficacy. The preferred embodiments of the instant invention address all five of these objectives where the background art does not.

Dilation balloons are also commonly used to deploy stents or stent-grafts. Even further, many stents or stent-grafts are configured with a multi-stranded, braided, sleeve or tube. One of the descriptions of the present invention is similar to that of the braided sleeve. Hence, the present device can be used such that the stent or stent-graft can be mounted on the inner/outer system described below and when put into compression; the stent or stent-graft expands radially (just as it does when it is mounted on a dilatation/deployment balloon). Alternatively, when the tubular braid dilatation system is used, the system could be modified so that the tubular braid is 'detachable' from the elongate shaft of the catheter or wire. In this case, it could be left in place as a stent or stent-graft. The 'detachable' tubular braid could be put into compression so that it expands. This may be accomplished by having reinforcements on both sides of the tubular braid that can be moved inward relative to one another to cause the compressive force on the tubular braid. Once the forces are withdrawn, the tubular braid would remain in place in the vessel. Additional dilation from a balloon could be added now to 'set' the stent or stent-graft in place. Often, a stent or stent-graft only needs a 'nudge' to start its expansion both in the case of self-expanding and balloon expanding endoprostheses.

For these reasons, it is desirable to provide improved devices that may circumvent some of the problems associated with previous techniques. This improved medical device provide a new configuration that will eliminate some of those problems and methods for their use, which facilitate removal of vascular and other vessel obstructions, narrowing, constrictures, disease prevention, etc. in the operating room or interventional suite.

SUMMARY OF THE INVENTION

In a first embodiment of the present invention provides an improved device (guide wire or catheter) of the type having an elongate flexible shaft with a proximal end and a distal end. The improvement comprises configuring at least a distal portion of the flexible shaft so that it can assume a shape(s) along its shaft (proximally, mid-section or distally) that will act as a dilator. This guide wire or catheter can be moved along the lumen (artery, vein, intestine, stent, graft, or other hollow vessel or organ, etc.) and to the obstruction area (clot, plaque, or other obstruction). Once it is in the vicinity of the obstruction/constrictionlnarrowing, the user (physician/technician) can easily actuate the dilation mechanism(s) so that it is enlarged beyond its original size/diameter and dilate the narrowed passageway. Further, a similar mechanism can be deployed distal to the obstruction so that when the dilatation is occurring and fragments are dislodged during the therapy, the distal mechanism can trap them from moving downstream. These emboli can be trapped and then obliterated or removed at some later time.

A second embodiment of the instant invention, concerned with delivery or a drug/agent/solvent to the vessel wall, is directed to a tubular device, which has proximal and distal ends, constructed of monofilament or multifilament braids for use in the vascular system of the body. The braid, in a collapsed configuration, is elongated and would fit over the deflated balloon of an angioplasty catheter in a relaxed manner. Although it may be essentially the same length as the angioplasty balloon (or other dilatation device), it would likely extend proximal to and distal to the balloon on the shaft of the catheter, being of greater length than the balloon. It may extend to the distal tip of the catheter and may be affixed to the catheter shaft at or near the tip, either permanently or releasably. It may also be affixed to the catheter shaft proximally. It may have an attachment for engagement by a guide wire at its distal end or may be affixed to a wire or thread proximally. As will become apparent subsequently, a means for deploying the braid device and un-deploying, or contracting, the device other than the balloon may be necessary.

In a preferred version of this embodiment, the braids are made of a material, which has physical properties, which allow absorption of fluids or drugs into the braid material in the relaxed or non-expanded configuration. This would be performed outside the body before insertion of the device. After insertion and when the dilatation device is distended/expanded, the braid would expand with the device or as part of the device, be placed into a stretching tension and be compressed against the vessel wall. These two forces, stretching and compression, will cause the fluid, drug, solvent or other therapy residing within the absorbent material of the braid to be displaced from the braid. This agent would the diffuse into the wall, in the case of the passive diffusion configuration. In the case of the active transport system, electrical charges would be utilized to either draw the agent into the wall or to pump the agent into the wall. Similarly, the agent could be located between the dilatation mechanism and the outer braid or other material coating the dilatation mechanism.

Alternatively, the braid may be constructed of tiny tubular filaments, which may not have absorbent properties. However, because these filaments are tubular in nature, fluids containing drugs or other materials may be injected into them and delivered through them to the vessel wall. It is obvious that a means of injecting fluid into the filaments, such as another lumen in the catheter carrying the device, may be necessary. In addition, the exit site of the tubular filaments could take the form of small holes, porous material, slits, or just weakened areas of the filaments, just to name a few configurations. The tubular design of the filaments of the braid would also add strength to the device so that the outward radial forces needed for scaffolding purposes, described below, would be enhanced.

The braid may have other physical properties other than absorbency. The braid may possess enough rigidity to remain expanded after the initial balloon distention, providing scaffolding to prevent, or significantly lessen, elastic recoil of the dilated vessel. The braid is multi-stranded and may be either mono or multifilament braid.

Additionally, the aforementioned tubular braided mechanism is easily adapted for use at the exit site for a long term or indwelling catheter or other tube. This exit site is problematic for a variety of reasons; the most important of which is that it is a site when infection can occur. By using the tubular braid with the aforementioned disease inhibiting characteristics, the problems of this 'exit site' are greatly reduced. It is a simple matter to manufacture the yarns/strands of the tubular braid using bio-resorbable materials well known to the medical device industry such as, but not limited to de-hydrated collagen strands. These strands readily absorb solvents/solutions and concurrently could be designed to be reabsorbed by the body in a pre-determined period of time.

While the device is augmented with several novel features to reduce disease and facilitate the angioplasty procedure, i.e., local drug delivery, scaffolding, ridges causing microfractures, flow through the porous braid, and single catheter insertion, any one of these features may be used alone or in combination with any of the other features to inhibit disease and facilitate the angioplasty procedure.

As well, while the discussions have addressed the uses of the device within the vascular system, the device may be utilized in the form described, or in a modified form, within other passageways in the body for local delivery of drugs, radiation, and other materials, scaffolding, hemostasis, disease treatment or prevention as well as other uses.

BRIEF DESCRIPTION OF THE DRAWINGS

FIG. 1-A is an illustration of a standard angioplasty catheter 1 with a standard angioplasty balloon 4. In this illustration, the angioplasty balloon 4 is shown un-inflated as shown by the wrinkles 5 on the un-inflated balloon 4 located near the distal end 3 of the device. This drawing is not exemplary of any preferred embodiment of the instant invention, but rather serves as a platform for additional FIGS. 1-B through 4. It is important to note that this drawing is only a representation of all angioplasty catheters and is not intended to be specific. In this figure as well as all other figures where an angioplasty balloon 4 is represented, specific design parameters have not been added such as the Y-Port adapter/valve that would usually be on an angioplasty balloon catheter. Such a Y-Port is usually used for feeding a guide wire through the axial port and subsequent inflation/deflation of the balloon through the Y port. Said Y-Port is located on the proximal end 2 of the device 1.

FIG. 1-B is an illustration of angioplasty balloon catheter of the present invention where a material 7 has been placed over the balloon 4 to trap drugs or other agents or therapy during said angioplasty. The drawing illustrates braid 7 covering the balloon 4, however the instant invention describes other materials other than braid. Further, the angioplasty balloon 4 is completely covered in the drawing with the material. Complete coverage is not mandatory for the instant invention

FIG. 3 is a schematic illustration of an embodiment of the instant invention whereby the combination catheter of FIG. 2 is located in a narrowed vessel of the body.

FIG. 4 is a schematic illustration of an embodiment of the instant invention whereby that by moving an inner wire or mandril in the direction of the arrow, the distal aspect of the guide wire enlarges so that it may engage the distal aspect of the device to expand the mechanism there.

Figure 2:
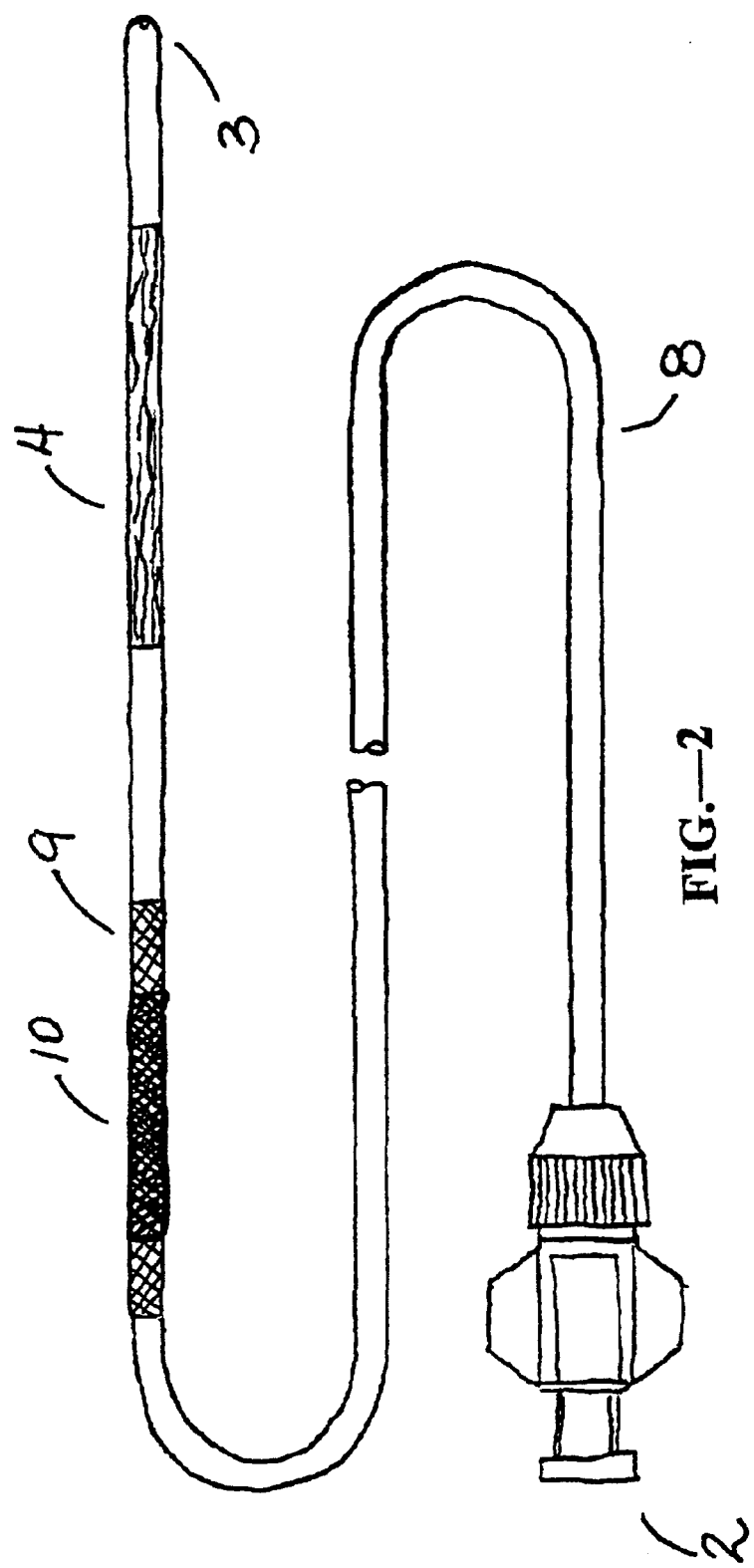
FIG. 2 is an illustration of one preferred embodiment of the instant invention where an angioplasty balloon 4 and another mechanical dilator or deployment mechanism 9 is located on the same catheter/device 8. In this figure, a stent 10 is also located on the proximal mechanical dilator/deployment mechanism 9.

These illustrations show only some potential configurations of the present invention. Other parametric changes of the present invention can occur such as location of the described elements on the distal portion of the device as well as the actual type of mechanism(s) used. The location of these mechanisms may vary from the proximal to the distal end although all figures illustrate a distal location. Further, specific design parameters that are not pertinent to the instant invention are not delineated in the figures such as, but not limited to guide wires, valves, syringes, proximal deployment means, etc.

DESCRIPTION OF THE EXEMPLARY EMBODIMENTS

The present invention is used for intervention into the tubular channels (arteries, veins, biliary tract, urological tract, gastro-intestinal tract, stents, grafts, sinuses, nasopharynx, heart, ears, etc.) or hollow cavities (stomach, gall bladder, urinary bladder, peritoneum, etc.) of the body. Further, it may be used in iatragenically created passageways. It is particularly convenient to use in an environment of an operating room, surgical suite, interventional suite, Emergency Room, patient's bedside, etc. One preferred embodiment of this device is that the elongate, flexible shaft is inserted into the tubular channel or hollow cavity of the body usually through pecutaneous access or via a surgical incision. In the case of lumens that enter and exit the body naturally, the device may enter through one of those entry or exit paths (i.e. rectal opening, mouth, ear, etc.). Once the device is in the preferred location (that being where the narrowing or obstruction is located), the expandable dilation mechanism(s) is deployed (usually actuated by the physician outside the body) so that the configuration(s) on the device opens/deploys. As the dilating mechanism is expanded, it pushes outward with a radial force that dilates or compresses the tissue. In the case of blood vessels, this is often referred to as PTA (Percutaneous Transluminal Angioplasty).

The deployment mechanism(s) on the system can be configured so that it is 'detachable' so that when dilation has occurred, the mechanism(s) (or part of it) can be left in place for scaffolding of the passageway. This scaffolding is often referred to as an endoprosthesis, stent or stent-graft. Even further, a stent or stent-graft (or other scaffolding prosthesis) can be mounted onto the mechanism(s) and then left in place post deployment/dilation. The dilator mechanism(s) described herein are usually inserted into the patient in an un-deployed (smaller) fashion. It may arrive in the package in a deployed or un-deployed state.

Referring to FIG. 1-A, illustrated is a standard dilatation catheter. This particular catheter 1 is a balloon catheter as is illustrated by the un-inflated balloon 4 located near the distal end 3 of the catheter 1. The proximal end 2 of the catheter is generic and does not specify other parameters usually seen with a balloon dilatation catheter. For instance, not illustrated is the usual Y-Port that is located near the proximal end 2 of the catheter. The balloon 4 of this figure is shown un-inflated or deflated in the illustration as is represented by the wrinkles 5 in the balloon 4. The wrinkles in the wall of the empty balloon indicated that likely an inelastic material is used to make the balloon 4. However, the instant invention may use an elastic, relatively inelastic or inelastic material for the balloon. FIG. 1-A is an illustration of a nonspecific dilation device to serve as a basis for delineating the preferred embodiments of the instant invention.

Turning now to FIG. 1-B, a dilation catheter 6 of the instant invention is illustrated. In this embodiment, tubular braid 7 is mounted near the distal end 3 of the catheter 6. In this illustration, the tubular braid 7 is mounted over a dilation balloon 4. The dilatation balloon 4 is difficult to see in the drawing due to the braid 7 covering it. However, the tubular braid 7 alone could be illustrated whereby no balloon 4 is required. In such a case (in contrast to inflating a balloon), the braid would likely be put into a compressive state to expand the tubular braid 7 radially outward In FIG. 1-B, the tubular braid 7 may be made of an absorbent material so that a drug, agent or other therapy can become impregnated or absorbed into the individual yarns of the braid or within the interstitial spaces between the braid or in the space between the braid 7 and the balloon 5. Further, a coating (not shown) could be applied over or within the braid to accomplish the same. When such an agent is used and the dilatation device 7 or 5 is radially expanded into the narrowed tissue, the agent can be delivered 'locally' to the narrowed tissue. Additionally, the exterior material on the dilatation mechanism may have coarse or otherwise characteristics so that the material will have a tendency to be greater or otherwise impregnated into the narrowed tissue. This may have several advantages. It may help disturb the organized matrix of the tissue that is narrowed. Further, it may help deliver the therapy deeper into the narrowed tissue. Even further, it may help keep the agent in the narrowed tissue during the dilation period. This may be particularly useful in a dynamic flow situation such as in the case of PTA where blood flow may be present during dilatation.

Turning now to FIG. 2, another embodiment of the instant invention is illustrated. In this drawing, an elongate device 8 with two separate dilators (4 and 9) is shown. The device 8 shows two dilation mechanisms located near the distal end 3 of the device. The most distal dilation mechanism illustrated in this figure is a dilatation balloon 4. Somewhat proximal to the balloon is a second dilatation mechanism 9. The proximal dilatation mechanism 9 illustrated here is a tubular braid type. Again, radial expansion outward of the dilatation mechanism 9 is usually accomplished by putting the tubular braid into a compressive state. Further, mounted onto the proximal dilatation mechanism 9 is a scaffolding endoprosthesis 10 often referred to as a stent or stent-graft. It is noted that the stent and stent deployment is not illustrated here. One embodiment of the instant invention is that the device 8 will be inserted into a narrowed space, usually with the aid of a guide wire (not shown) and when the distal dilatation mechanism 4 is radially expanded, the narrowed space is expanded. Once the space is somewhat enlarged, the device 8 is moved forward so that the proximal dilatation mechanism 9 and endoprosthesis 10 are oriented into the area. The proximal dilation mechanism 9 is then expanded radially so that the endoprosthesis 10 is deployed into the once narrowed area to help keep the area propped open or otherwise scaffolded. It is important to note that the dilation mechanisms 4 and 9 on device 8 can be interchanged with respect to location along the device 8. Further, the device may have two balloon dilatation mechanisms or two other types of dilatation mechanisms. Further, the tubular braid 7 or 9 may be designed so that is 'detachable' from the device 8 so that it may act as both the dilator 9 and the endoprosthesis 10 or either.

Referring now to the dilation mechanism 9, a multi-stranded (mono or multi filament) tubular braid, also referred to as braided sleeving is illustrated. When the braid is put into compression, the braid is pulled together and it flares out to create a larger diameter. Alternatively, either the braid or the other mechanism (like the malecot mechanism described below) can have a permanent set put into in so that it is normally open with the larger diameter. In this case, when it is put into tension (usually from some inner (or outer) core wire or mandril), it collapses down to the diameter of the shaft of the device 8. Alternatively when these 'normally open/deployed' mechanisms could be constrained to a smaller 'unopened' diameter with a slideable over tube. This braided sleeve/tubing described is similar to a common child's toy of years ago, known as Chinese Finger Cuffs. In this case, when the tubular braided sleeve is pushed together, the braided assembly enlarges radially. It can enlarge with significant outward radial force. Hence, this outward radial force can cause the dilation. Further, this braided configuration can have a roughened surface that may be very useful in breaking up the matrix of the stenosis. In other words, as mentioned above in the prior art, the braid can act as a cutter as would the tiny cutters on the balloon. Further, because the braid may be porous, drugs or other therapies can be dispensed during dilatation or other placement (in the case of an exit site catheter/device for example). Further, the interstitial porosity allows other mechanisms to be passed through the wall of the braid for therapy.

Alternatively, too much abrasive action on the surface of the dilatation mechanismn(s) may be deleterious to the patient as well. In the case of the braided configuration, some smoothener may be required so that just the appropriate amount of surface roughness is realized for effective matrix disorganization/disruption. This surface covering could be total or partial covering of the device as required for the particular application. Further, the realized rigidity of any of the type of mechanism(s)s must be optimized for the particular application. Even further, this smoothener added to the tubular braid may aid a receptacle for holding the agent or as a porous membrane for the agent to pass through.

The expansile mechanism of the dilation system can be fabricated from several materials and configurations. The strands (of the braid) can be made of any material that would be useful for a particular application (polymers like polyester, nylon, Mylar, etc.) or, metal (stainless steel, Nickel Titanium Alloy (Nitinol), platinum, etc.). The same is true for the malecot (not illustrated and described below). Certainly, the materials of the present invention are not constrained to those materials listed. Additionally, the mechanism may be coated or encased in an elastomeric, inelastic or other covering. Further, the mechanism may be fabricated of a material that will enlarge due to different forces than that of the braid mentioned previously. One other such force derived mechanism could be a material that swells/enlarges when put into a moist environment. Another such forced derived mechanism is one that swells/enlarges when put in a temperature differential. Yet, another may be one that occurs from an electrical, magnetic or other mechanical configuration/design/force. The dilation mechanisms could be radially expanded in their relaxed state or radially compressed in their relaxed state.

Another preferred embodiment of the present invention is the availability of different porosities. This is critical. As the braid is made up of filaments, the porosity can be varied. This can allow drugs to be passed through the wall (which is made up of individual filaments). Equally important or maybe more important, when conventional dilating balloons are used, the vessel is totally occluded for the period of therapy that dilation is occurring. As previously, mentioned, lavish perfusion balloons have been developed so that perfusion (blood flow) can occur during dilation. As one expands the braid (or the malecot), as it expands to its fullest diameter, the porosity on the outer wall decreases and becomes 'solid' in nature. However, both ends of the expanding braided mechanism remain porous. Hence while the dilation is occurring, blood can flow through the dilating member.

Further, as mentioned briefly above, the filaments of the braid (or malecot) change orientation, as they are expanded/enlarged. This changed orientation may be helpful in breaking up the matrix of the underlying disease. Further, the porosity of the braid (or malecot) changes during the dynamics of the enlarging process. This too may be helpful in that the filaments will 'grab' part of the intimal wall while enlarging/expanding. Further, it will continue to grab the inner wall and stress it or change it somehow so that re-stenosis is greatly decreased.

The tubular braid may be coated with a material so that it may have no porosity or variable porosity within the individual filaments of the braid. With one technique the braid was expanded from its original small diameter by sliding a mandril into the tubular braid. Once the braid is expanded, a liquid thermoset elastomer including, but not limited to silicone rubber, latex rubber, etc. or thermoplastic material including, but not limited to polyurethane was coated via a spray, dip, brush or other method. When the material cured, the mandril was removed and the tubular braid could be pulled on both ends (put into compression) and the tubular braid would go back to its original diameter. This is important for several reasons; the method described here allows the material to be applied within the filaments instead of over the filaments. This decreases the overall diameter of the tubular braid significantly as opposed to putting a covering over it. Further, the integrity of the material in between the filaments as opposed to over the filaments is increased because as the expandable channel is pushed forward, the material is hidden within the braid and hence doesn't see the forces of the tissue against it. Using a covering over the braid, the forces during the pushing are directly transmitted to the covering over the braid. Even further, the reliability and cost to manufacture are greatly improved. Even further and of extreme import is the fact that using a liquid that cures or a thermoplastic covering that is melted into the braid as opposed to covering it allows for avarying the porosity along the tubular braid. This is extremely important in those cases where variable porosity is desired such as when the device is being used for a filter such as in the case of trapping emboli that are loosened during interventional vascular procedures to name one instance. In this case the emboli could travel into the device where the pore size is large, but not pass through the device where the pore size is less. The emboli could then be removed once the device is un-deployed.

Several different types of tubular braid were coated with silicone rubber elastomer. In one case, the braid was expanded to some diameter greater than the relaxed and smaller diameter. This was accomplished using a Teflon mandril. With the tubular braid in this somewhat expanded condition, the assembly was coated with liquid silicone rubber. When it dried, the assembly could be elongated by putting the system into tension so that the smaller original diameter was achieved again. It could then be put into compression and thusly shortened so that it would expand and the braid was covered so that there could be no holes in between the filaments of the braid. Further, the overall diameter of the tubular braid was not increased except for maybe 0.0001". Even further, filter devices were made whereby the silicone rubber was sprayed or painted onto the tubular braid when it was in the deployed/expanded condition. Once dried, the assembly could be un-deployed and then re-deployed with ease and without any holes between the filaments. Lastly, tubular braids were coated as described above with only partial coating to create variable porosity along the braid. Even further, the totally coated tubular braid was easy to puncture so that variable porosity was achieved as well.

Producing a roughened surface on the film within the braided devices is easily accomplished in the manufacturing environment. One such way is to create bubbles in a liquid slurry of the polymer prior to its solid curing. Another might be the addition of dissolvable crystals to the surface of the liquid polymer prior to its cure. These dissolvable crystals could then be removed (washed off) after curing of the polymer.

The assembly of tube, mandril and braid is.

As taught, possible configurations of the distal mechanism(s) are varied. Illustrated is tubular braid 9 or 7 and balloon 4 mechanisms. Another such mechanism and a preferred embodiment of the present invention use a configuration known as a malecot (not illustrated). This malecot is a common configuration used in catheters for holding them in place (in the case of feeding tubes in the intestines or stomach). It is usually a polymeric (but may also be metal) tube that has more than one, but usually two or more slits symmetrically opposed. When the distal tip of the malecot is put into compression (usually by pulling an inner wire or mandrel or tube), the sides of the polymer are pushed outward so as to create a larger diameter on the distal tip. This enlarged distal malecot diameter is larger than the body/shaft of the device. In the case of this malecot type mechanism, the surface of the malecot could be roughened or a separate membrane (attached or not) could be put over or under the malecot so that it is roughened or strengthened or added for another reason.

Turning now to FIG. 3-A, the device 8 of FIG. 2 is partially illustrated in a narrowed blood vessel 11. The narrowing of the blood vessel 11 is indicated by the formation of plaque 12 attached to the intimal lining 13 of the vessel. The device 8 has been inserted into the body and blood vessel 11 until the distal dilation mechanism 4 is oriented appropriately in the narrowed space. In this figure, the dilatation mechanism is a dilatation balloon 4. The device 8 and balloon 4 are oriented to the correct location with the aid of image intensification (x-ray, ultrasound, MRI, etc.). Once in the appropriate location, the dilation mechanism is deployed/dilated to expand the narrowed vessel 11. This dilatation process is not illustrated. Once complete the dilatation mechanism 4 is un-deployed and the catheter/device 8 is advanced further into the vessel as illustrated in FIG. 3-B. The plaque 12 of FIG. 3-A has been compressed and the vessel is somewhat expanded so that the narrowing is decreased. This compressed plaque 15 has a tendency to recoil so often an endoprosthesis/stent/stent-graft 10 is desired to be placed into the dilated vessel 14 to help keep it propped open. Once the second dilation/deployment mechanism 9 is oriented appropriately in the dilated vessel 14, it is deployed. In FIG. 3-B the second dilation mechanism illustrated is a tubular braid 9 with a stent 10 mounted onto it. Once deployed, the stent 10 remains in place in the newly dilated vessel 14. It may be desired to pull the device 8 backward just enough so that the first dilatation mechanism, in this case a balloon 4, is oriented near the position of the newly implanted stent 10. In this case, the first dilatation mechanism 4 can be dilated (inflated) a second time to further expand and/or embed the stent 10 into the dilated wall 16 of the vessel 14. In fact, this is often the case in normal practice for the interventionalist, especially in the case where self-expanded stents are used.

The scaffold 10 and or the dilating mechanisms 9 or dilating mechanism 4 is preferably coated with a medical grade substance having low thrombogenicity or other medicament that helps prevent deleterious effects that may accompany these procedures. Alternatively, the scaffold 10 may be coated with any of a variety of fabrics/textiles that allow tissue growth into it, other stabilization or other preferred characteristic. Further, the scaffold 10 or dilating mechanisms 4 and 9 may be impregnated with radioactivity, monoclonal anti-bodies or a variety of other medicaments that may inhibit re-stenosis or other deleterious effects that wish to be avoided. Further, the braid can be coated with an elastomer or plastically deformable material so that it might go from a small size to a large size and the interstitial spaces are coated with some porous or non-porous material. One, but certainly not the only way to accomplish this coating is to first dilate the braid to a larger diameter by placing an inner rod or mandril inside the tubular braid/braided sleeving. At this point, the assembly is coated with a liquid dispersion and allowed to dry/volatilize. Once dry, the inner rod is removed and the system can be put into tension and the diameter will decrease to the original small diameter. This process can be accomplished by impregnating the tubular braid with a thermoplastic material as well as thermoset.

Turning now to FIG. 4, an embodiment of the instant invention is illustrated where the dilation mechanism is a tubular braid/braided sleeving 9. In the case of a dilator only, the distal end 17 of tubular braid 9 is bonded to the distal end 17 of the inner wire or tube 20. The proximal end 18 of the tubular braid 9 is bonded to the outer tube 19 which will likely end at 18. In one preferred embodiment, moving the inner mandril or tube 20 relative to the outer tube 19 to expand the dilator 9 actuates the dilator. In another preferred embodiment, a second outer tube (not shown) can be slid over the dilation mechanism to keep it in the smaller diameter and then removed to allow it to expand. This might be the deployment mechanism used when the normal relaxed condition of the dilator is in the expanded/larger condition.

Turning now to FIG. 4-B, the inner mandril or tube 20 has indeed been moved relative to the outer tube 19 as indicated by the arrow 21. The dilating mechanism is thus expanded as indicated by 22. The mechanism illustrated in FIG. 4 is a tubular braid mechanism, however, the malecot design could also be used.

Drawings of the device of the present invention are included in the appendix. An exemplary device has the following characteristics:

Working Length

10–500 cm

Working Diameter

The inner wire/mandril of the present invention has an outer diameter that ranges from 0.006 to 0.150 inches, usually in the range of 0.008 to 0.035 inches but can extend to smaller and larger sizes as technology and procedures require. The outer tube/shaft of the instant invention has an inner diameter that will accept the inner wire/mandril, an outer diameter in the range of 0.020 top 0.400 inches usually in the range of 0.030 to 0.200 inches but can extend to smaller and larger sizes as technology and procedures require. The dilation mechanism of the present invention would be small in its un-deployed state (similar to that of the wire or tube mentioned above, depending on the configuration), but would be expandable to diameters of 0.010 to 0.500 inches, but usually in the range of 0.030 to 0.400 inches, but can extend to smaller and larger sizes as technology and procedures require or even larger. The dilatation mechanism will usually have two diameters, a smaller/undeployed diameter which would be in the range of 0.010 to 0.100 inches or even larger. The larger/deployed state of the mechanism may extend from 0.050 to 2.00" inches or even larger depending upon the vessel being dilated.

Physical Configuration

The device of the present invention may have conventional lubricious coatings to enhance introduction into the target body lumen, e.g. hyaluronic or other equivalent coatings. Further, the technician may apply a lubricious coating just prior to surgery. As an advantage of the present invention, the device will be less difficult to feed it to the desired location in the body due to its decreased size. Another advantage of the present invention would be the ease with which obstructions can be snared for removal or obliteration. This decreased difficulty will decrease cost due to time in the Operating Room (Operating Rooms costs are estimated in excess of $90 dollars per minute in the U.S.) Additionally, there will be realized a decrease in difficulty for perfusion during treatment that will aid in patient care/recovery and the potential in deleterious effects due to the total occlusion during conventional treatment.

An exemplary device having dilating mechanism(s) located on its distal tip is illustrated in FIGS. 1–4. The mechanism(s) may be at the tip or somewhere else in the distal portion of the device or even in the middle of the device. Additionally, this mechanism(s) may be any of a number of mechanisms that will help aid in dilating the tissue. In all FIGS. 1–3, the dilation mechanism/system is illustrated in its un-deployed condition. In FIG. 4-B, it is in its deployed condition.

As previously mentioned, emboli can become loosened during many of these therapies and these emboli can have deleterious affects 'downstream'. This occurrence would appear to be increased with a LIS approach due to the fact that in an open procedure, the site of revision is in direct view so that this particulate should be more easily detected and removed. Conversely, in a LIS procedure the physician is dependent upon image intensification and his or her actual skill to not allow emboli from being dislodged and causing 'downstream', distal problems. The instant invention may likely be used with a distal protection system as described.

It is an object of the invention to provide a catheter/device for deploying an endoprosthesis/stent/stent-graft.

It is yet a further object of the invention to provide an endoprosthesis deployment device or guide wire with the added ability to dilate the narrowed passageway using the same device.

It is still a further object of the invention to provide a system for dilating a narrowed passageway.

It is another object of the present invention to allow the dilating mechanism to have an irregular surface for disturbing the matrix of the narrowed intima of the tissue to aid in the therapy.

It is another object of the present invention to allow perfusion through the dilating mechanism.

It is another object of the present invention to allow delivery of drugs, energy, mechanisms, etc. through or into the walls of the dilating mechanism to aid with such therapies.

It is still a further object of the invention to provide a system for allowing the delivery of a drug or other therapeutic agent to the dilatation site at the time of dilatation and this iteration is described below. The preferred version of this embodiment relies on a passive system of drug delivery, in concert with the objectives to keep the device simple, inexpensive, and easy to operate.

The passive system for delivery of the drug or other agent will rely primarily on diffusion of the concentrated drug into the vessel wall. An active system may use a process referred to as iontophoresis, which because of a differential in electric charges essentially pumps the drug into the vessel wall and perivascular soft tissues. One embodiment employs a novel method of iontophoresis, which uses the normal negative resting potential of the heart and the normal depolarization/repolarization cycle to draw the drug into the vessel wall and perivascular tissues.

The device is simply soaked in a container of fluid which contains a drug or other material, absorbing a quantity of the fluid determined by the size and composition of the braid and, to a lesser extent, the type of fluid. The fluid may contain any drug or other material approved for use within the body by the Food and Drug Administration. The device, including the angioplasty balloon, is inserted into the blood vessel, the angioplasty balloon positioned appropriately, and the balloon inflated in a standard manner. The distention of the angioplasty balloon stretches and compresses the braid so that the braid releases the fluid containing the drug or other material adjacent to the arterial wall, where it is absorbed into the arterial wall by passive diffusion.

Alternatively, an active transport mechanism may be provided to better facilitate the transfer of the drug or material into the vessel wall. One active transport system is Iontophoresis, which uses a differential in electrical charges to either pull the drug or material into the vessel wall or to pump it from the inner surface of the vessel into the vessel wall. The configuration of the electrodes within the device, the catheter, or the body may take any one of several forms. There may be an external electrode on the patient's body and an internal electrode within the braid device or the angioplasty catheter. There may be two internal electrodes, one within the braid device and one within the angioplasty catheter. The electrodes may be placed elsewhere, i.e., on the guiding catheter or on the guide wire. In the case of a stent, the stent may act as an electrode and the second electrode may be incorporated into any one of the locations described. One configuration involves a single electrode in the braid device or any of the other locations, and uses the normal negative resting potential of the heart to draw the drug or material into the vessel wall. In fact, there may be any combination of the above configurations.

It is likely that, in the case of intracoronary iontophoretically enhanced drug delivery; the device will be synchronized with the electrocardiogram to deliver tiny pulses of electrical charge. These pulses may be delivered in the depolarization phase, the repolarization phase, the resting phase, or the refractory phase or period. A separate programmable device would control the delivery time, amplitude, voltage, current, etc., and the synchronization with the electrocardiogram.

The operator would initiate the iontophoretic components at the onset of balloon inflation, typically, although initiation after or during balloon inflation is also possible. If the braid device remains expanded after the initial balloon dilatation, the iontophoretic components may be activated continuously even after the angioplasty balloon is deflated. This will allow the process to continue while allowing for blood flow through the site of the lesion because of the porous nature of the braid device. In the case of the passive diffusion configuration, the braid device will maintain contact with the vessel wall continuously, allowing more material to diffuse into the vessel wall.

The braid device will also act as scaffolding to prevent elastic recoil during the balloon deflations. This is secondary to the radial forces caused by the braid device being shortened during the balloon inflation. Therefore, the braid device would diminish elastic recoil by acting as scaffolding and because of the micro-fractures caused in the plaque matrix. These microfractures would disrupt the structure of the plaque it would not tend to reassume its pre-dilated shape.

Moreover, the present invention may be utilized with a stent to provide pharmacological and mechanical means of combating re-stenosis. A self-expandable or balloon expandable stent may be used, and the stent may or may not be designed and packaged for use with the device. Additionally, the device may have the properties of a scaffold or stent and actually act as means to mechanically counteract the forces of elastic recoil without the presence of a separate stent.

While the discussion centers on braid design, it is the express intent that this patent should cover any material whether braided, woven, molded, pressed, sliced, compressed, expanded, or any other material which has the capacity to absorb a drug or other substance containing a physiologically active ingredient, and release that drug or material when compressed. For example, the device may be constructed of a sponge material or foam material, which would absorb the drug or other substance, and then release that drug or material when compressed by the expanding balloon. In fact, some other force other than compression may accomplish the release of the absorbed drug or material.

As mentioned above, the texture of the braid over the angioplasty balloon will create tiny micro-fractures within the plaque matrix which will reduce damage to the vessel wall, diminish the incidence of dissections, diminish the elastic recoil of the wall, and allow for more uniform compressibility of the plaque. All of these factors have been implicated in the re-stenosis process. This action, even without the drug delivery features, may diminish re-stenosis. However, by creating the tiny micro-fractures within the plaque, the drug is able to be delivered in a better proximity to the vessel wall than without this property. The braid will likely become slightly and temporarily imbedded within the micro-fractures of the plaque, creating a desirable situation which enhances delivery of the drug or material into the plaque and vessel wall because of proximity, and, concomitantly, decreases the amount of drug or material which is washed away by the flowing blood.

The operator would inflate the angioplasty balloon a single or multiple times, while simultaneously delivering the drugs, fracturing the plaque, and preserving the distention of the lesion with the braid device. As one can see from the foregoing description of the preferred embodiment, the drug delivery and other actions are accomplished essentially during the angioplasty procedure and there is no need for a second catheter insertion to deliver the drug or other material or to effect the other actions of the device with the embodiment described. Obviating the need to reinsert another catheter to accomplish this action saves a significant amount of time, expense, and potential risk to the patient. However, in another embodiment, the drug delivery and other actions could be performed with a device separate from the angioplasty catheter or on another balloon on or separate from the initial angioplasty catheter. In still another embodiment, the actions could be performed in concert with a stent deployment. The operation of these other embodiments will not be described, but are similar to the operation of the preferred embodiment.

The un-deployment or contraction of the braid device from the vessel wall deserves special attention since the braid device will not contract to its original state when the balloon is deflated, at least in the preferred embodiment in which it acts as a scaffold while the balloon is deflated. The braid device may be returned to its original low profile shape over the deflated angioplasty balloon by one of several means, which by mention, are incorporated into the present invention.

The distal end of the braid device may be constructed so that it engages a guide wire, so that by advancing the guide wire, withdrawing the catheter, or a combination of these motions, the braid device elongates and returns to its original undeployed shape and state. The guide wire may contain an expanded portion that will engage the braid device or there may be a portion of the guide wire, which expands because of traction on an inner core of the guide wire. This expandable portion of the guide wire may be constructed of a flexible braid or other material.

The braid device may be collapsed or contracted by holding the catheter in place and pulling on a wire or thread attached to the proximal portion of the braid device. Alternatively, if the braid device were affixed to the catheter shaft proximal to the balloon, simply withdrawing the catheter would cause the braid device to disengage the vessel wall and elongate.

Still another means of collapsing the braid device after use may be to use a shaped memory alloy within the braid. The shaped memory alloy would be formed so that it would cause the braid to seek a collapsed, elongated, tubular shape after expansion when the distending balloon is deflated. This alloy may be used as a filament within the braid, but also may be disposed as longitudinal lay-ins between the braided filaments. Horizontal lay-ins may also be utilized to aid in returning the braid device to its original undeployed state. A combination of any of the collapsing means may be used, as well.

Further, it is yet another object of the instant invention to provide a novel prosthesis/tissue interface that prevents, treats or inhibits disease during implantation such as long term indwelling catheters which may be used to inhibit or treat re-stenosis or disease. This is a device to be used on any long term indwelling catheter in the lumens or cavities of the body at the site the catheter exits the patients skin. There is a need to stabilize the catheter and prevent its withdrawal and to promote healing of the skin around the exit site to prevent infection, irritation, need for daily care, weeping, inability to shower, etc. The exit site device of the instant invention addresses and solves these problems with a unique expandable braid of collagen yarns which can be attached to the synthetic material of the catheter and will allow the ingrowth of skin into the device. In other words, the skin will not grow into or attach itself to the foreign catheter material directly. This new exit site device in constructed so it can be affixed to the catheter and the skin will then grow into the device creating a seal between the skin and the catheter. This exit site device is usually constructed of a braid, similar to the drug delivery device above, and is meant to be placed over or on the catheter just beneath the skin. The purpose of this device is to encourage the skin to heal over the catheter and produce a tight seal preventing the ingress of bacteria, fungus, and contaminants into the catheter tract. The indwelling catheter creates a crevice in the tissues and the epidermis tends to grow down this tract, frequently carrying bacteria with them. This results in infection in the catheter tract. This device would create a bond between the skin and the catheter utilizing braided crosslinked collagen attached to the outer portion of the catheter in a tubular matter. The collagen lattice will provide an optimal framework for the ingrowth of normal tissues, which would be affixed to a membrane, such as silicone, which in turn, would be affixed to the catheter. If the device were constructed from a braid, foreshortening the braid would cause diametric expansion of portions of the braided device, causing it to initially assume a football like shape and subsequently a plate like shape, depending on the forces applied. This would cause an anchor like effect within the tissues and prevent movement of the catheter. Alternatively, the device may be constructed of material other than collagen and may not necessarily be of braided construction. A spiral or helical configuration is possible and this patent is to cover any expansile configuration, i.e., the device maintains a low profile shape upon insertion but is changed to a diametrically expanded shape after insertion for anchoring purposes. The preferred embodiment, being a braided collagen device, may have only one end of its tubular configuration attached to the catheter. Forcing the non-attached end of the tubular braid toward the attached end will cause the braid to deform into the shapes above. Alternatively, the device may be in a football or plate-like shape initially, and tension may be required to cause it to assume a tubular shape for insertion, for example.

The features of the invention believed to be novel are set forth within the description of this disclosure. However, the invention themselves, both as to organization and method of operation, together with further objects and advantages thereof may best be understood by reference to the following description taken in conjunction with the accompanying drawings.

The Tubular Braid or Braided Sleeve Element

The braided sleeve or tubular braid apparatus described herein include an expandable tubular braid. In the case of the dilating apparatus, an inner mandril or wire may be used to contact the tubular braid. The elongate mandril extends from the proximal end of the device to the distal end of the tubular braid. The distal end of the tubular braid is bonded/attached to the distal end of the inner elongate mandril. The mandril may extend beyond the tubular braid. The proximal end of the tubular braid is bonded to the distal end of an elongate tube. In the case of the drug delivery element, the tubular braid may or may not be attached to the substrate catheter. In this case, the tubular braid will be used as a means to deliver the drug or other agent to the lesion or to break up the matrix of plaque in the lesion.

The braid may be open, but may be laminated or covered with a coating of elastic, generally inelastic, plastic or plastically deformable material, such as silicone rubber, latex, polyethylene, thermoplastic elastomers (such as C-Flex, commercially available from Consolidated Polymer Technology), polyurethane and the like. Further, the inventors of the instant invention have disclosed a method of coating the interstitial pores of the tubular braid without adding to the overall wall thickness of the tubular braid. This manufacturing invention is disclosed in pending provisional submission U.S. Ser. No. 60/121,640. The assembly of tube, mandril and braid is introduced percutaneously in its radially compressed state. In this state, the outside diameter of the braid is close to the outside diameter of the elongate tube. This diameter is in the range of 10 to 50 mils, and usually 25 to 40 mils (i.e. thousandth of an inch). After insertion, moving the mandril proximally with respect to the tube expands the tubular braid.

The tubular braid is preferably formed as a mesh of individual non-elastic filaments (called "yarns" in the braiding industry). Nevertheless, it can have some elastic filaments interwoven to create certain characteristics. The non-elastic yarns can be materials such as polyester, PET, polypropylene, polyamide fiber (Kevlar, DuPont), composite filament wound polymer, extruded polymer tubing (such as Nylon II or Ultem, commercially available from General Electric), stainless steel, Nickel Titanium (Nitinol), or the like so that axial shortening causes radial expansion of the braid. These materials have sufficient strength so that the engaging element will retain its expanded condition in the lumen of the body while removing the obstruction therefrom. In the case where the tubular braid is used as an absorbent material for drug or other agent delivery, the individual filaments may be absorbent in nature or as stated earlier, the drug or other agent may be merely trapped in between the tubular braid and the underlying dilating member.

The braid may be of conventional construction, comprising round filaments, flat or ribbon filaments, square filaments, or the like. Non-round filaments may be advantageous to decrease the axial force required for expansion to create a preferred surface area configuration or to decrease the wall thickness of the tubular braid. The filament width or diameter will typically be from about 0.5 to 25 mils, usually being from about 5 to 10 mils. Suitable braids are commercially available from a variety of commercial suppliers.

The tubular braids are typically formed by a "Maypole" dance of yarn carriers. The braid consists of two systems of yarns alternately passing over and under each other causing a zigzag pattern on the surface. One system of yarns moves helically clockwise with respect to the fabric axis while the other moves helically counter-clockwise. The resulting fabric is a tubular braid. Common applications of tubular braids are lacings, electrical cable covers (i.e. insulation and shielding), "Chinese handcuffs" and reinforcements for composites. To form a balanced, torque-free fabric (tubular braid), the structure must contain the same number of yarns in each helical direction The tubular braid may also be pressed flat so as to form a double thickness fabric strip. The braid weave used in the tubular braid of the present invention will preferably be of the construction known as "two dimensional, tubular, diamond braid" that has a 1/1 intersection pattern of the yarns which is referred to as the "intersection repeat". Alternatively, a Regular braid with a 2/2 intersection repeat and a Hercules braid with an intersection repeat of 3/3 may be used. In all instances, the helix angle (that being the angle between the axis of the tubular braid and the yarn) will increase as the braid is expanded. Even further, Longitudinal Lay-Ins can be added within the braid yarns and parallel to the axis to aid with stability, improve tensile and compressive properties and modulus of the fabric. When these longitudinal "Lay-In" yarns are elastic in nature, the tubular braid is known as an elastic braid. When the longitudinal yarns are stiff, the fabric is called a rigid braid. Biaxially braided fabrics such as those of the present invention are not dimensionally stable. This is why the braid can be placed into an expanded state from a relaxed state (in the case of putting it into the compressive mode). Alternatively this could be a decreased/reduced (braid diameter decreases) state when put into tension from the relaxed state. When put into tension (or compression for that matter) the braid eventually reaches a state wherein the diameter will decrease no more. This is called the "Jammed State". On a stress strain curve, this corresponds to increase modulus. Much of the engineering analysis concerning braids is calculated using the "Jammed State" of the structure/braid. These calculations help one skilled in the art to design a braid with particular desired characteristics. Further, material characteristics are tensile strength, stiffness and Young's modulus. In most instances, varying the material characteristics will vary the force with which the expanded condition of the tubular can exert radially. Even further, the friction between the individual yarns has an effect on the force required to compress and un-compress the tubular braid. For the present invention, friction should be relatively low for a chosen yarn so that the user will have little trouble deploying the engaging element This is particularly important when the engaging element is located a significant distance from the user. Such is the case when the percutaneous entry is the groin (Femoral Artery for vascular interventions) and the point of engaging the engaging element is some distance away (i.e. the Carotid Artery in the neck). Similarly, this is true for long distances that are not vascular or percutaneous applications.

Therefore, in summary, the use of the device is relatively simple and adds little time to the procedure and potentially a significant benefit to the patient. The drug or other material is delivered at the same time and with the same catheter as the angioplasty and the device is removed with the angioplasty balloon, in the preferred embodiment. In addition, other actions occur at this time (scaffolding and microfractures) which also contributes significantly to inhibit the re-stenosis process.

While preferred embodiments of the present invention have been described in detail, it is apparent that modifications or adaptations of the embodiments will occur to those skilled in the art. It is to be expressly understood, however, that such modifications and adaptations are within the scope of the present invention.

What is claimed is:

1. A method for dispensing an agent into body tissue defining a passageway of a body for treatment of cardiovascular disease comprising:

positioning a porous tubular braid having individual yarns, comprising a contact-dispensable agent in contact with all of the individual yarns, at a target site within the passageway of the body the porous tubular braid defining an open interior;

expanding the tubular braid against the body tissue by a separate radially-expandable element within the open interior or the tubular braid causing the tubular braid to make intimate contact with the body tissue;

dispensing the agent from the tubular braid into the body tissue;

contracting the radially-expandable element and the tubular braid from the body, and removing the radially-expandable element and the tubular braid from the body.

2. The method according to claim 1 wherein the expanding step is carried out using a balloon.

3. The method according to claim 1 further comprising:

selecting an absorbent fiber tubular braid;

selecting the agent; and applying the agent to the absorbed fibers of the tubular braid prior to the positioning step.

4. The method according to claim 1 wherein the dispensing step is carried out as a result of the expanding step.

5. The method according to claim 1 wherein the positioning step is carried out using a porous tubular braid which is not bioabsorbable.

6. A method for dispensing an agent into body tissue defining a passageway of a body for treatment of cardiovascular disease comprising:

positioning a porous tubular braid, having individual yarns, comprising a contact-dispensable agent in contact with all of the individual yarns, at a target site within the passageway of the body the porous tubular braid defining an open interior;

expanding the tubular braid against the body tissue by a separate radially-expandable element within the open interior of the tubular braid causing the tubular braid to make intimate contact with the body tissue;

dispensing the agent from the tubular braid into the body tissue, the dispensing step being carried out using Iontophoresis; and removing the radially-expandable element and the tubular braid from the body.

* * * * *